United States Patent [19]

Jaeger

[11] Patent Number: 4,559,944
[45] Date of Patent: Dec. 24, 1985

[54] SURGICAL INSTRUMENT FOR GYNECOLOGICAL PROCEDURES

[76] Inventor: John C. Jaeger, 3584 Batavia-Elba TLR, Oakfield, N.Y. 14125

[21] Appl. No.: 597,053

[22] Filed: Apr. 5, 1984

[51] Int. Cl.⁴ ............................................. A61B 17/28
[52] U.S. Cl. .................................... 128/344; 128/344
[58] Field of Search ............... 128/321, 322, 344, 778, 128/17; 604/96, 97, 98, 99, 102

[56] References Cited

U.S. PATENT DOCUMENTS

| | | | |
|---|---|---|---|
| 75,693 | 3/1868 | Morrell | 604/96 |
| 2,601,513 | 6/1952 | Gladstone | 128/321 |
| 4,083,369 | 4/1978 | Sinnreich | 128/344 |
| 4,192,313 | 3/1980 | Ogami | 128/321 |
| 4,430,076 | 2/1984 | Harris | 128/344 |

*Primary Examiner*—Gene Mancene
*Assistant Examiner*—Cary E. Stone
*Attorney, Agent, or Firm*—Lalos, Keegan, Marsh, Bentzen & Kaye

[57] ABSTRACT

A surgical instrument for performing gynecological procedures comprising a first forceps lever having a forwardly disposed section insertable into a vaginal cavity, an intermediate section and a rearwardly disposed handle section, a second forceps lever having a forwardly disposed section insertable into a vaginal cavity with the insertable section of the first forceps lever, an intermediate section pivotally connected to the intermediate section of the first forceps lever and a rearwardly disposed handle section cooperable with a handle section of the first forceps lever, the insertable section of the first forceps lever having a longitudinally disposed bore, a plunger member disposed in the longitudinally disposed bore and displaceable longitudinally therein, such plunger member being insertable in the uterine canal when the insertable sections of the forceps levers are inserted into a vaginal cavity, flexible material disposed on the plunger member and expandable to engage the wall of the uterine cavity and provide an expansive bearing contact therewith, and the insertable section of the second forceps lever having a lip portion engageable with the cervix of the uterus when the insertable sections of the forceps levers are inserted into a vaginal cavity, the plunger member is inserted in the uterine canal and the handle sections are moved together, thereby causing the uterine cervix to be clamped between the forceps levers.

29 Claims, 4 Drawing Figures

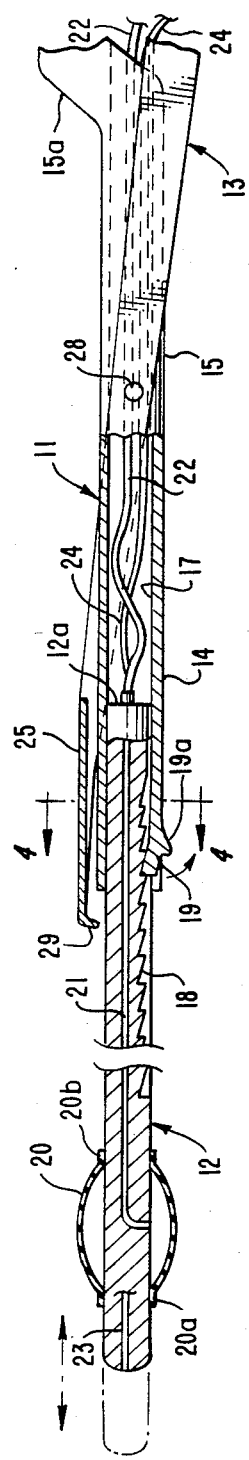
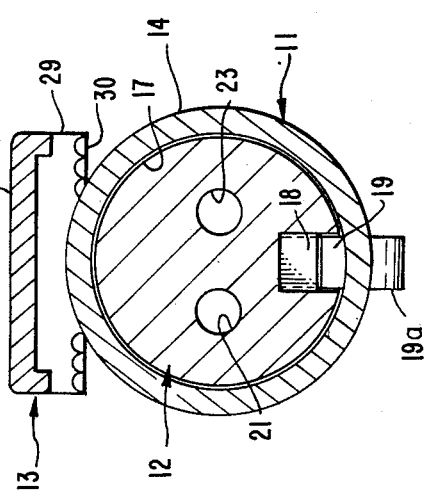

SURGICAL INSTRUMENT FOR GYNECOLOGICAL PROCEDURES

BACKGROUND OF THE INVENTION

This invention relates to a surgical instrument and more particularly to an instrument used in performing gynecological procedures.

In certain gynecological procedures, it often is necessary to reposition the uterus or to inject a fluid into the uterus for performing diagnostic procedures such as in a diagnostic laparoscopy. In procedures requiring the repositioning of the uterus, it has been the conventional practice of gynecologists to use uterine grasping forceps which are provided with a member which is inserted into the uterine canal and a member having an end portion which engages the uterine cervix in clamping relation to permit the physician to firmly grasp the uterus and manipulate it to the desired position. Because of the usually narrow configuration of the member inserted into the uterine cavity, the manipulation of the forceps can result in injury to the uterus. Occasionally, in such procedures, the wall of the uterus is perforated during manipulation.

In procedures requiring the injection of a fluid into the uterus, it has been the practice of gynecologists to use a uterine cannula which includes a member insertable into the uterine canal for supplying the fluid to be injected into the uterus and a collar type of element mounted on the insertable member which engages the wall of the uterus to prevent the fluid being injected into the uterine canal from flowing backwardly into the vagina.

Conventional uterine cannulas have been found not to be entirely satisfactory in that upon injection of the fluid into the uterus, the fluid will occasionally leak past the occlusion in the uterine canal provided by the collar like element, into the vagina, or cause the occluding device to become dislodged and the instrument flushed out of the uterine canal, resulting in the loss of fluid and an interruption in the diagnostic procedure.

It thus has been found to be desirable to provide an instrument for manipulating the position of the uterus and also for injecting a fluid into the uterus for diagnostic purposes which will obviate the aforementioned inadequacies of prior art instruments.

Accordingly, it is the principal object of the invention to provide a novel surgical instrument.

Another object of the present invention is to provide a novel surgical instrument suitable for use in performing gynecological procedures.

A further object of the present invention is to provide a novel surgical instrument suitable for use in certain gynecological diagnostic and treatment procedures.

A still further object of the present invention is to provide a novel surgical instrument suitable for use in repositioning the uterus.

Another object of the present invention is to provide a novel surgical instrument suitable for use in firmly gripping the uterus to permit the manipulation of the uterus into a desired altered position.

A further object of the present invention is to provide a novel surgical instrument suitable for use in firmly gripping and manipulating the position of a uterus without causing injury to the uterus.

A still further object of the present invention is to provide a novel surgical instrument suitable for firmly gripping and manipulating the uterus, having a component thereof insertable in the uterine canal which will not cause perforations of the wall of the uterine canal as the instrument is manipulated to change the position of the uterus.

Another object of the present invention is to provide a novel surgical instrument for injecting a fluid into the uterine canal.

A further object of the present invention is to provide a novel surgical instrument for injecting a fluid into the uterus having means for occluding the uterine canal to prevent the loss of fluid into the vagina.

A still further object of the present invention is to provide a novel surgical instrument for injection fluid into the uterus, having means for occluding the uterine canal to prevent the flow of fluid into the vagina, in which the fluid is effectively prevented from leaking past the occluding device.

A still further object of the present invention is to provide a novel surgical instrument for injecting a fluid into the uterus having means for occluding the uterine canal in which the fluid being injected into the uterus will not dislodge the occluding device and cause the instrument to be flushed into the vagina.

Another object of the present invention is to provide a novel surgical instrument for injecting a contrast fluid into the uterus in diagnostic laparascopy.

A further object of the present invention is to provide a novel surgical instrument suitable for use in performing gynecological procedures which is simple in design, effective in performance and comparatively inexpensive to manufacture.

Other objects and advantages of the present invention will become more apparent to those persons having ordinary skill in the art to which the invention relates from the following description taken in conjunction with the accompanying drawings.

BRIEF DESCRIPTION OF THE DRAWINGS

FIG. 3 is an enlarged side elevational view of the instrument illustrated in FIG. 1, having portions thereof broken away; and FIG. 4 is an enlarged cross-sectional view taken along line 4—4 in FIG. 3.

DESCRIPTION OF THE PREFERRED EMBODIMENTS

Figure 1:
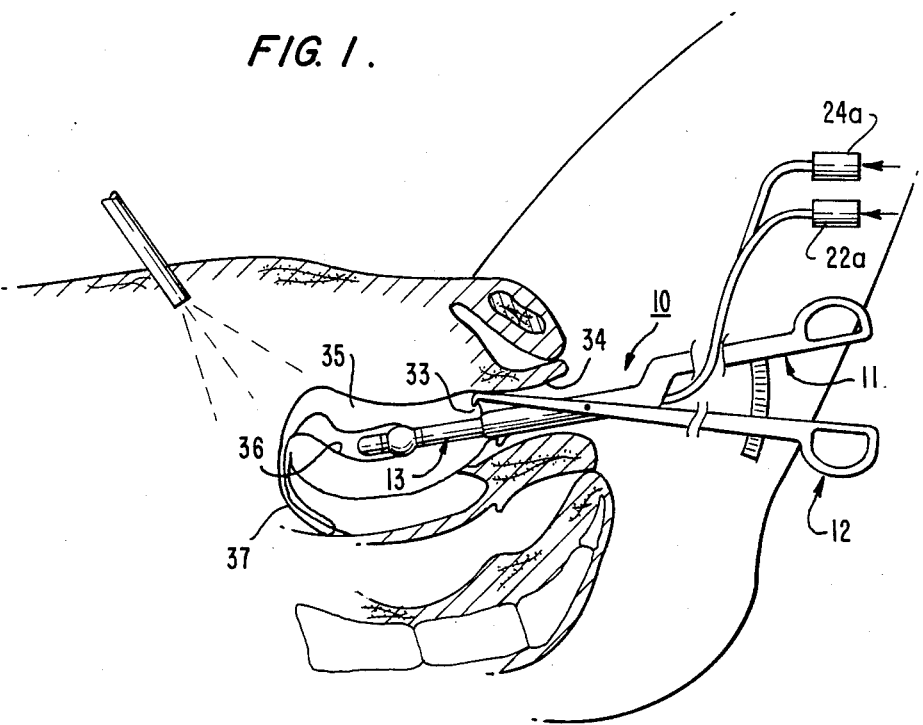
FIG. 1 is a side view of an instrument embodying the present invention, shown inserted in the female gential tract for performing diagnostic laparascopy.

Referring to the drawings, there is shown a surgical instrument 10 for manipulating the position of the uterus or injecting a fluid into the uterus which generally consist of a first or main lever member 11, an extension or plunger member 12 mounted in main lever member 11 and a second or clamping lever member 13 pivotally connected to the main lever member. Lever member 11 includes a forwardly disposed section 14 and intermediate section 15 having a portion disposed at an angle as at 15a and a rearwardly disposed handle section 16 offset relative to forwardly disposed section 14. As best shown in FIG. 3, the forwardly disposed and intermediate sections 14 and 15 of lever 11 are provided with a longitudinally disposed cylindrical bore 17 for receiving the plunger member.

As best illustrated in FIGS. 3 and 4, plunger member 12 consists of an elongated cylindrical member which is received within and longitudinally displaceable in longitudinally disposed bore 17 of lever member 11. The length of the plunger member is greater than the length of bore 17 to accommodate the insertion of the plunger member through either the front or rear end of bore 17 and the adjustment of its displacement relative to the forwardly disposed section 14 of lever member 11. As best shown in FIG. 3, an underside of the plunger member is provided with a ratchet configuration 18 which cooperates with a pawl element 19 preferably formed integrally with the front end portion of section 14 of lever member 11 for restraining the displacement of the plunger member relative to lever member 11, thus permitting the setting of the exposed length of the plunger member. The pawl element 19 is provided with a projection 19a which permits the pawl element to be manipulated by the finger or an instrument to retract the pawl in setting the position of the plunger member.

Plunger member 12 is intended to be inserted in the uterine canal of a patient undergoing diagnosis or treatment and is provided with a balloon or bladder 20 which is adapted to be expanded when the plunger member is positioned in the uterine canal to engage the wall of the uterus. The forwardly disposed portion of the plunger member extends through bladder 20 and the openings in the bladder receiving the plunger therethrough are provided with annular portions 20a and 20b which are secured about the periphery of the plunger preferably by a suitable adhesive. The bladder may be formed of any flexible, expandable material which will not adversely react with any adbominal structure. To accommodate the insertion and removal of the plunger into and out of bore 17, the diameter of the plunger may be made slightly smaller than the diameter of bore 17 or bladder 20 can be mounted on a recessed portion of plunger 12 so that the deflated balloon will pass easily through bore 17 without interference or binding.

Air under pressure is supplied to bladder 20 for expanding the bladder by means of an internal passageway 21 intercommunicating the interior of bladder 20 and a port provided on a rear face 12a of the plunger and a fluid supply line 22 communicating with fluid passageway 21, extending through and out of the rear end of bore 17 and having a connector 22a connectable to a source of air under pressure. Fluid to be injected into the uterus is supplied through a passageway 23 extending through the entire length of the plunger member and fluid supply line 24 communicating with passageway 23, extending through and out of the rear end of bore 17 and having a connector 24a adapted to be connected to a source of the fluid to be injected into the uterus.

Figure 2:
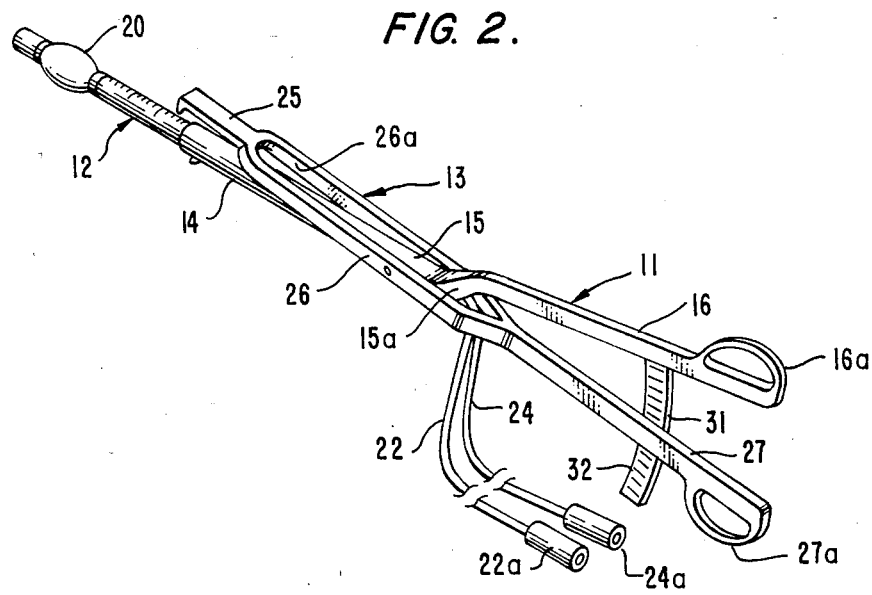
FIG. 2 is an enlarged, perspective view of the instrument illustrated in FIG. 1.

Referring to FIGS. 2 and 4, it will be seen that clamp lever 13 includes a forwardly disposed insertable section 25 and intermediate section 26 and a handle section 27. The intermediate section thereof is provided with an elongated opening 26a which receives the intermediate section of lever member 11 therethrough. The lever members are pivotally connected together by means of a set of transversely aligned pins 28, each of which projects through a side segment of intermediate section 26 into registered openings in intermediate section 15 of lever member 11. A split pin arrangement is utilized for pivotally connecting the lever members together to permit unobstructed passage of the plunger member through longitudinal bore 17 when the plunger is inserted into the bore through the rear end thereof. The forward end of section 25 extends beyond the forward end of section 14 of lever member 11, as best illustrated in FIG. 3, and is provided with a downwardly projecting lip portion 29. The lip portion is provided with a transversely disposed, serrated edge 30 which is adapted to cooperate with an upper surface of plunger member 12 to clamp the instrument onto the uterine cervix when the plunger is inserted in the uterine canal. The clamping action of the lever members is provided by moving handle sections 16 and 17 together in the usual manner. To facilitate the clamping and unclamping of the instrument, the handle sections thereof are provided with finger rings 16a and 27a. In addition, for restraining the angular displacement of the lever members relative to each other about the axis of pivot pins 28, handle section 16 is provided with an arcuately shaped projection 31 having a surface 32 engaged by handle section 27. In the conventional manner, the frictional engagement of handle section 27 with the knurled or otherwise coarse surface 32 will restrain the angular displacement of the lever members but will allow such displacement upon being manipulated by the fingers of the user.

In the use of the instrument as described for repositioning the uterus, the depth of the uterine canal of the patient is first determined by sounding. The instrument is then prepared by inserting the plunging member in the cylindrical bore of lever member 11, adjusting the projected length of the plunger member in accordance with the measurement of the uterine cavity depth, connecting connector 22 to the source of air under pressure and moving the handle sections of the instrument together to move the insertable section 25 of lever member 13 adjacent the plunger as best illustrated in FIG. 3. Then, with the patient positioned as illustrated in FIG. 1 and the cervix 33 having been dilated, the plunger and insertable sections 14 and 25 are inserted into the vagina 34 with the forward end of the plunger being guided through the dilated opening of the uterus 35 into the uterine canal 36. After the entire length of the projecting portion of the plunger is fully inserted into the uterine canal, the instrument is backed off slightly, the handle sections are moved slightly apart to displace the serrated edge 30 relative to the plunger, the instrument is then moved slightly forward and the handle sections are moved together to clamp the cervix between serrated edge 30 and an upper surface of the plunger with the projecting portion of the plunger fully inserted in the uterine canal. With the instrument thus positioned, a suitable valve is operated to supply air under pressure through fluid line 22 and passageway 21 to inflate balloon 20. As the balloon inflates and the outer wall thereof expands, it will engage the wall of the uterine canal to provide a large bearing surface with the plunger being retained in spaced relation to the uterine wall.

With the instrument thus positioned, as shown in FIG. 1, the physician may then manipulate the instrument to reposition the uterus into the desire position. In doing so, the clamping engagement of lip portion 29 with the cervix will prevent the instrument from becoming dislodged, and the engagement of the balloon wall with the wall of the uterine cavity will permit the application of pressure on the uterine wall without risk of perforation. It will be appreciated that the engagement of the flat, broad surface of the balloon wall will transmit the maneuvering forces to the wall of the uterine without bringing the plunger itself into undue or damaging contact with the wall.

In performing a diagnostic laparoscopy with the use of the instrument as described, the patient is prepared in essentially the same manner as previously described except that the patient is placed under a light general anesthesia, the abdomen is inflated to extend the abdominal wall and a laparoscope is inserted through a small incision in the abdominal wall into the abdominal cavity for observing the pelvic region. The instrument is inserted and secured in the patient in the manner as previously described. After the uterine canal is occluded by the inflation of balloon 20, and connector 24a is connected to a source of contrast fluid, a suitable valve is operated to cause the contrasting fluid to behavior through fluid line 24, passageway 23 and the uterine cavity into the fallopian tubes 37. With the contrast fluid thus flowing through the fallopian tubes, the physician may examine the flow of the contrast fluid by means of the laparoscope in the conventional manner.

During the laparoscopy, the firm grip of the instrument on the uterus provided by the clamping action of lip portion 29 engaging the cervix, will prevent the dislodgement of the instrument as the contrast fluid is injected into the uterine canal and any flushing of the plunger out of the uterine canal into the vagina with a corresponding loss of contrast fluid. In addition, the engagement of the wall of the balloon with the wall of the uterine cavity will prevent leakage of contrast fluid between the plunger and the wall of the uterine canal and the loss of fluid into the vagina.

To remove the instrument from the patient, the supply of contrast fluid is shut off, the balloon is permited to deflate, the handle sections of the instrument are moved apart to release the cervix and the entire instrument is then withdrawn from of the patient.

The various components of the instrument as described can be fabricated from any suitable materials. The levers and plunger may be fabricated from a metallic material such as stainless steel or a plastic material such as a clear polyvinyl chloride material. The components may be formed of materials suitable for repeated use or may be made of disposable materials. In addition, the lever members of the instrument can be made for reuse and the plunger may be made to be disposable. As an example, the lever members may be made of stainless steel and reused after normal sterilization procedures and the plunger may be made of a plastic material such as a clear polyvinyl chloride material which may be disposed of after use. The balloon portion of the plunger also can be made of any suitable material compatible with clinical conditions required under the circumstances.

Although the embodiment of the invention as described provides for the plunger receiving bore 17 extending through lever member 11 so that the plunger may be inserted either through the front or rear end of the bore, it is contemplated that such bore need not extend entirely through such lever member. Under circumstances where the bore does not extend entirely through the lever member, however, it further is contemplated that a suitable opening would be provided in lever member 11 so as to pass the air and contrast fluid supply lines therethrough, although other arrangements may be employed to conduct such supply lines to the exterior for connection to the proper systems for supplying the air and contrast fluid.

With regard to the configurations of the insertable sections and handle sections of the lever members and the plunger member, although rectilinear configurations have been shown, it is contemplated that such sections and components may be curved to facilitate the insertion and removal of the instrument during its use. Also, it is contemplated that the outer surface of the plunger be provided with measurement markings, preferably in centimeters, to permit the physician's technician to properly adjust the projected length of the plunger in accordance with the measurement of the depth of the uterine cavity taken in advance by sounding methods.

From the foregoing detailed description, it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

I claim:

1. A surgical instrument suitable for use in performing gynecological procedures comprising a first forceps lever having a forwardly disposed section insertable into a vaginal cavity, an intermediate section and a rearwardly disposed handle section, a second forceps lever having a forwardly disposed section insertable into said vaginal cavity with the insertable section of said first forceps lever, an intermediate section pivotally connected to the intermediate section of said first forceps lever and a rearwardly disposed handle section cooperable with the handle section of said first forceps lever, said insertable section of said first forceps component having a longitudinally disposed bore, a plunger disposed in said longitudinally disposed bore and displaceable longitudinally therein, insertable in the uterine canal when the insertable sections of said forceps levers are inserted into said vaginal cavity, means disposed on said plunger and expandable to engage the wall of said uterine canal and provide an expansive bearing contact therewith, and the insertable section of said second forceps lever having a lip portion engageable with the cervix of the uterus when the insertable sections of said forceps levers are inserted in said vaginal cavity, said plunger is inserted in said uterine canal and said handle sections are moved together causing the cervix to be clamped to said instrument.

2. A surgical instrument according to claim 1 including means opratively interconnecting said first forceps lever and said plunger for restraining the longitudinal displacement of said plunger relative to the insertable section of said first forceps lever.

3. A surgical instrument according to claim 2 wherein said restraining means comprises a pawl and ratchet mechanism.

4. A surgical instrument according to claim 1 including means operatively interconnecting said handle sections for restraining the angular displacement of said handle sections between each other relative to the axis of the pivotal connection between said forceps levers.

5. A surgical instrument according to claim 4 wherein said handle restraining means includes a portion of one of said handle sections having a contact surface slidably engageable by the other of said handle sections to frictionally hold said handle sections in selected angular relationships.

6. A surgical instrument according to claim 1 wherein the longitudinally disposed bore in the insertable section of said first forceps lever extends from a front end thereof, a predetermined distance into said section, and said plunger has a length greater than the length of said bore.

7. A surgical instrument according to claim 1 wherein the longitudinally disposed bore in the insertable section of said first forceps lever extends through the entire length of said section thereby permitting the insertion and removal of said plunger into and out of said bore to and from the front and rear ends thereof.

8. A surgical instrument according to claim 7 wherein the length of said plunger is greater than the length of said bore.

9. A surgical instrument according to claim 1 wherein said expandable means comprises an inflatable bladder.

10. A surgical instrument according to claim 9 including fluid supply means communicating with said inflatable bladder and communicable with a source of pressurized fluid.

11. A surgical instrument according to claim 10 wherein said fluid supply means includes a fluid passageway in said plunger communicating with the interior of said bladder and a fluid supply line communicating with said fluid supply passageway and communicable with a source of pressurized fluid.

12. A surgical instrument according to claim 9 wherein said plunger extends through said bladder so that upon inflation of said bladder, the bladder will expand away from the periphery of the plunger to engage the periphery of the wall of the uterine canal and maintain said wall in spaced relation to said plunger.

13. A surgical instrument according to claim 12 including fluid supply means communicating with said inflatable bladder and communicable with a source of pressurized fluid.

14. A surgical instrument according to claim 13 wherein said fluid supply means includes a fluid passageway in said plunger communicating with the interior of said bladder and a fluid supply line communicating with said fluid passageway and communicable with a source of pressurized fluid.

15. A surgical instrument according to claim 1 wherein said plunger includes a fluid passageway for conducting and injecting a contrast fluid into the uterus when said plunger is inserted in the uterine canal, said expandable means has been expanded to engage the wall of the uterine canal to form an occlusion of the uterine canal and said handle section have been moved together to clamp the cervix between the forceps levers, and contrast fluid supply means communicating with said fluid passageway and communicable with a source of said contrast fluid.

16. A surgical instrument according to claim 1 wherein the intermediate section of said second forceps lever includes an opening through which the intermediate section of said first forceps lever is received.

17. A surgical instrument according to claim 16 wherein said opening in the intermediate section of said second forceps lever is elongated along the length thereof.

18. A surgical instrument according to claim 17 wherein the handle section of said first forceps lever is offset relative to the insertable section thereof to accommodate the movement of said handle sections relative to each other.

19. A surgical instrument according to claim 1 wherein the length of the insertable section of said second forceps lever is greater than the length of the insertable section of said first forceps lever whereby said lip portion of the insertable section of said second forceps lever is cooperable with said plunger to clamp the uterine cervix therebetween.

20. A surgical instrument according to claim 1 wherein the lip portion of the insertable section of said second forceps lever is provided with a transversely disposed serrated edge engageable with the uterine cervix.

21. A surgical instrument according to claim 1 wherein said handle sections include finger rings.

22. A surgical instrument according to claim 1 wherein at least portions of said insertable sections of said forceps levers are curved to facilitate insertion.

23. A surgical instrument according to claim 1 wherein at least portions of said handle sections of said forceps levers are curved to facilitate insertion of said insertable section.

24. A surgical instrument according to claim 1 wherein said forceps levers and said plunger are formed of a metallic material.

25. A surgical instrument according to claim 1 wherein said forceps levers and said plunger are formed of a plastic material.

26. A surgical instrument according to claim 1 wherein said forceps levers and said plunger are formed of disposable materials.

27. A surgical instrument according to claim 1 wherein said forceps levers are formed of a metallic material and said plunger is formed of a disposable material.

28. A surgical instrument according to claim 1 wherein said forceps levers are formed of stainless steel and said plunger is formed of a clear polyvinyl chloride material.

29. A surgical instrument according to claim 1 wherein said plunger is provided with measurement markings along the length thereof.

* * * * *